US009254258B2

(12) United States Patent
Lewis et al.

(10) Patent No.: US 9,254,258 B2
(45) Date of Patent: *Feb. 9, 2016

(54) AMPHIPHILIC BLOCK COPOLYMERS FOR NUCLEIC ACID DELIVERY

(75) Inventors: Andrew Lennard Lewis, Farnham (GB); Giuseppe Battaglia, Sheffield (GB); Irene Canton, Sheffield (GB); Peter William Stratford, Farnham (GB)

(73) Assignee: BIOCOMPATIBLES UK LIMITED, Farnham Surrey (GB)

(*) Notice: Subject to any disclaimer, the term of this patent is extended or adjusted under 35 U.S.C. 154(b) by 366 days.

This patent is subject to a terminal disclaimer.

(21) Appl. No.: 12/991,321

(22) PCT Filed: May 14, 2009

(86) PCT No.: PCT/EP2009/055864
§ 371 (c)(1),
(2), (4) Date: Jan. 28, 2011

(87) PCT Pub. No.: WO2009/138472
PCT Pub. Date: Nov. 19, 2009

(65) Prior Publication Data
US 2011/0151013 A1    Jun. 23, 2011

(30) Foreign Application Priority Data

May 15, 2008   (EP) ..................................... 08156272

(51) Int. Cl.
| | |
|---|---|
| *A61K 9/51* | (2006.01) |
| *A61K 9/00* | (2006.01) |
| *C12N 5/071* | (2010.01) |
| *A61K 31/7105* | (2006.01) |
| *B82Y 5/00* | (2011.01) |
| *A61K 9/127* | (2006.01) |
| *A61K 48/00* | (2006.01) |
| *C12N 15/11* | (2006.01) |

(52) U.S. Cl.
CPC ............. *A61K 9/0019* (2013.01); *A61K 9/1273* (2013.01); *A61K 48/0041* (2013.01); *C12N 15/111* (2013.01); *C12N 2320/32* (2013.01)

(58) Field of Classification Search
USPC ......................................................... 424/450
See application file for complete search history.

(56) References Cited

U.S. PATENT DOCUMENTS

| | | | | |
|---|---|---|---|---|
| 6,224,903 | B1 * | 5/2001 | Martin et al. .................. | 424/450 |
| 6,852,816 | B2 * | 2/2005 | Lewis et al. ................... | 526/277 |
| 6,916,488 | B1 * | 7/2005 | Meier et al. ................... | 424/450 |
| 2005/0163743 | A1 * | 7/2005 | Lewis et al. .................. | 424/78.3 |
| 2006/0069203 | A1 * | 3/2006 | Lewis et al. ................... | 524/556 |

FOREIGN PATENT DOCUMENTS

| | | | |
|---|---|---|---|
| WO | WO-93/01221 | * | 1/1993 |
| WO | 03/074090 A2 | | 9/2003 |
| WO | WO-2007-106900 | * | 9/2007 |
| WO | WO-2008-070571 | * | 6/2008 |

OTHER PUBLICATIONS http://www.credoreference.com/entry/ehsdorland/oligonucleotide, 2007.*
http://www.credoreference.com/entry/chambdict/zwitterion, 2001.*
http://www.credoreference.com/entry/heliconhe/hydrolysis, 2010.*
Cristiano Giacomelli, et al., "Phosphorylcholine-Based pH-Responsive Diblock Copolymer Micelles as Drug Delivery Vehicles: Light Scattering, Electron Microscopy, and Fluorescence Experiments", Biomacromolecules, 2006, pp. 817-828, vol. 7.
J. K. W. Lam, et al., "Phosphorylcholine-polycation diblock copolymers as synthetic vectors for gene delivery", Journal of Controlled Release, 2004, pp. 293-312, vol. 100.
Mangesh C. Deshpande, et al., "Influence of polymer architecture on the structure of complexes formed by PEG-tertiary amine methacrylate copolymers and phosphorothioate oligonucleotide", Journal of Controlled Release, 2002, pp. 185-199, vol. 81.
J.F. Tan, et al., "Correlating Transfection Barriers and Biophysical Properties of Cationic Polymethacrylates", Biomacromolecules, 2007, pp. 448-454, vol. 8, No. 2.
J.F. Tan, et al., "Aggregation Behavior and Thermodynamics of Binding between Poly(ethylene oxide)-block-Poly(2-(diethylamino)ethyl methacrylate) and Plasmid DNA", Langmuir, 2006, pp. 3744-3750, vol. 22, No. 8.
Mangesh C. Deshpande, et al. "The effect of poly(ethylene glycol) molecular architecture on cellular interaction and uptake of DNA complexes", Journal of Controlled Release, 2004, pp. 143-156, vol. 97.
Uracha Rungsardthong, et al., "Copolymers of amine methacrylate with poly(ethylene glycol) as vectors for gene therapy", Journal of Controlled Release, 2001, pp. 359-380, vol. 73.
Albert S. Lee, "Structure of pH-Dependent Block Copolymer Micelles: Charge and Ionic Strength Dependence", Macromolecules, 2002, pp. 8540-8551, vol. 35, No. 22.
M. Vamvakaki, et al., "Synthesis of Controlled Structure Water-Soluble Diblock Copolymers via Oxyanionic Polymerization", Macromolecules, 1999, pp. 2088-2090, vol. 32, No. 6.
Y.T. A. Chim, et al., "Structural Study of DNA Condensation Induced by Novel Phosphorylcholine-Based Copolymers for Gene Delivery and Relevance to DNA Protection", Langmuir, 2005, pp. 3591-3598, vol. 21, No. 8.

(Continued)

*Primary Examiner* — Frederick Krass
*Assistant Examiner* — Celeste A Roney
(74) *Attorney, Agent, or Firm* — Sughrue Mion, PLLC

(57) ABSTRACT

The present invention provides a composition comprising vesicles and encapsulated within the vesicles, nucleic acid comprising less than 1000 nucleotides, wherein the vesicles comprise an amphiphilic block copolymer having a hydrophilic and a hydrophobic block.
Methods of forming vesicles and methods of delivering nucleic acid, in particular, iRNA into cells, are also provided.

8 Claims, 12 Drawing Sheets
(10 of 12 Drawing Sheet(s) Filed in Color)

(56) References Cited

OTHER PUBLICATIONS

Carmen Alvarez-Lorenzo, et al., "Biophysical Characterization of Complexation of DNA with Block Copolymers of Poly(2-dimethylaminoethyl) Methacrylate, Poly(ethylene oxide), and Poly(propylene oxide)", Langmuir, 2005, pp. 5142-5148, vol. 21, No. 11.

Hannah Lomas, et al., "Non-cytotoxic polymer vesicles for rapid and efficient intracellular delivery", Faraday Discussions, 2008, pp. 143-159, vol. 139.

Hannah Lomas, et al., "Biomimetic pH Sensitive Polymersomes for Efficient DNA Encapsulation and Delivery", Advanced Materials, 2007, pp. 4238-4243, vol. 19.

Jianzhong Du, et al., "pH-Sensitive Vesicles Based on a Biocompatible Zwitterionic Diblock Copolymer", Journal of American Chemical Society, 2005, pp. 17982-17983, vol. 127.

U.S. Appl. No. 12/991,349, filed Nov. 5, 2010, Giuseppe Battaglia.

U.S. Appl. No. 12/991,330, filed Nov. 5, 2010, Andrew Lennard Lewis, et al.

European Patent Office, "Communication Pursuant to Article 94(3) EPC," issued in connection with European Patent Application No. 09 745 804.6, dated Feb. 18, 2014.

* cited by examiner

Figure 9 - continued
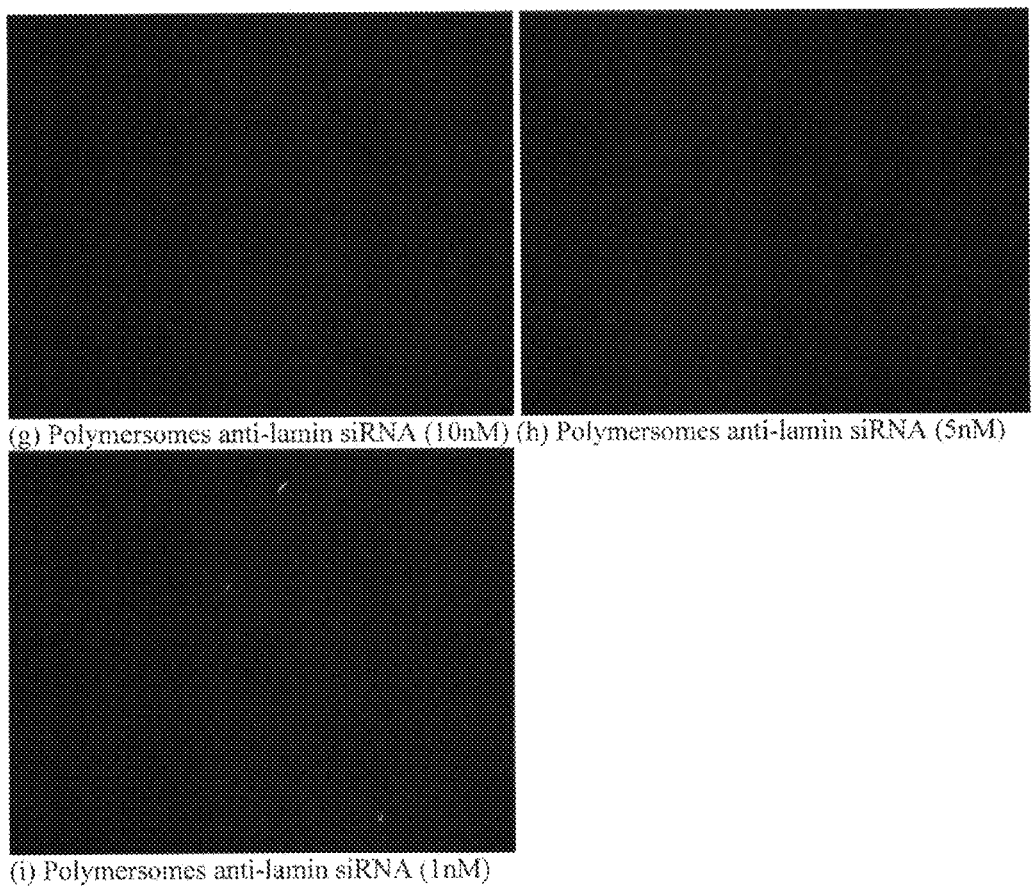
(g) Polymersomes anti-lamin siRNA (10nM) (h) Polymersomes anti-lamin siRNA (5nM)
(i) Polymersomes anti-lamin siRNA (1nM)

AMPHIPHILIC BLOCK COPOLYMERS FOR NUCLEIC ACID DELIVERY

CROSS REFERENCE TO RELATED APPLICATIONS

This application is a National Stage of International Application No. PCT/EP2009/055864 filed May 14, 2009, claiming priority based on European Patent Application No. 08156272.0 filed May 15, 2008, the contents of all of which are incorporated herein by reference in their entirety.

FIELD OF THE INVENTION

The invention relates to novel delivery systems for introducing nucleic acid into cells, more particularly RNA. Methods of delivering nucleic acid into cells also form part of the invention.

BACKGROUND OF THE INVENTION

Recently, researchers have tried to exploit the natural ability of RNAs to mobilize and transcript genetic information for therapeutic purposes. Such methods normally involve the interference with dysfunctional nucleic acids or proteins and/or the stimulation of the production of therapeutic genes. Particularly important is a process that uses synthetic double-stranded RNA, known as RNA interference (RNAi). This operates via post-transcriptional gene silencing, mediating the resistance to both endogenous parasitic and exogenous pathogenic nucleic acids, and therefore regulating the expression of protein-coding genes. It appears evident that the efficient cytosolic delivery of RNAs is a vital step in almost all RNAi-based gene-silencing experiments. Efficient cytosolic delivery of nucleic acids is, however, a very difficult task. Synthetic siRNAs can be delivered to cells in culture via electroporation or by using either cationic lipids or polymers. However, these approaches are limited by the transient nature of the response and in some cases by vector-mediated toxicity, (Mittal, V. Improving the Efficiency of RNA Interference in Mammals. *Nature Rev. Genet.* 5, 355-365 (2004)).

WO2002/044321 describes the sequence and structural requirements for small RNAs mediating RNA interference and therapeutic uses of interfering RNA. Using a drosophila in vitro system, it is demonstrated that 19-23 nucleotide short RNA fragments are the sequence-specific mediators of RNA.

Alnylam Pharmaceuticals Inc. have developed a variety of therapeutic compositions comprising siRNAs. Some of these are disclosed in, for instance, WO2004/030634. Sirna Therapeutics, Inc. are also active in this area. Their U.S. Pat. No. 7,022,828, for example, describes siRNA treatment of diseases or conditions related to levels of IKK-gamma.

EP1527176 describes novel forms of interfering RNA molecules. The molecules are double-stranded structures in which the strands are at least partially complementary to one another, and wherein the double-stranded structure is blunt ended. WO02006/069782, by the same Applicant, describes delivery agents for introducing small nucleic acids, such as those in EP1527176, into cells. The delivery agents are lipid compositions comprising a first lipid component, a first helper lipid and a shielding compound (for instance PEG) which is removable from the lipid composition under in vivo conditions.

We have recently reported on a very efficient, non-toxic and non-inflammatory vector for the delivery of (plasmid) DNA within human cells, (Lomas, H. et al. Biomimetic pH Sensitive Polymersomes for Efficient DNA Encapsulation and Delivery. *Adv. Mater.* Vol 19 (2007), 4238-4243). The combination of this type of polymer with DNA is described in our patent application WO03/074090. In this application, 2-(dimethyl) ethyl methacrylate (DMA)—MPC polymers are used to form DNA-polymer complexes. Depending upon the block lengths and pendant groups of the respective components of the copolymer, it is now known that the interaction with DNA can be tailored to produce DNA condensates (polyplexes) or have the DNA encapsulated within a vesicle of the material. The latter is based on the self-assembly of pH sensitive poly (2-methacryloxyethyl phosphorylcholine)-poly (2-(diisopropylamino)-ethyl methacrylate), (PMPC-PDPA) block copolymers into nanometer-sized vesicles, also known as polymersomes, (Du, J., Tang, Y., Lewis, A. L. & Armes, S. P. pH-Sensitive Vesicles Based on a Biocompatible Zwitterionic Diblock Copolymer. *J. Am. Chem. Soc.* 127, 17982-17983 (2005)).

Tan et al in Biomacromolecules 2007, 8, 448-454 describe polyethylene oxide-poly(dimethylamino)ethyl methacrylate (PEO-b-PDMA) and PEO-b-poly(diethylamino)ethyl methacrylate (PEO-b-PDEA) copolymers as a self-assembling non-viral vector for plasmid DNA delivery. Similarly, Tan et al in Langmuir vol, 22 No. 8, 2006, 3744-3750 describe complexes of PEO-b-PDEA copolymers with plasma DNA. Neither of these references discuss the formation of complexes with smaller strands of nucleic acid.

SUMMARY OF THE INVENTION

In view of the prior art there remains a desire to provide improved delivery systems for introducing nucleic acid comprising less than 1000 nucleotides into cells. In accordance with this desire there is provided in a first aspect of this invention a composition comprising vesicles and encapsulated within the vesicles, nucleic acid comprising less than 1000 nucleotides, wherein the vesicles comprise an amphiphilic block copolymer having a hydrophilic and a hydrophobic block.

The second aspect of this invention provides a method for forming a composition according to the first aspect of the invention, wherein one of the blocks of the copolymer is pH sensitive, comprising the steps:

(i) dispersing the amphiphilic copolymer in an aqueous media;
(ii) acidifying the pH of the composition formed in step (i);
(iii) adding the nucleic acid to the composition; and
(iv) raising the pH to around neutral to encapsulate the nucleic acid.

The third aspect of this invention provides an in vitro method of delivering nucleic acid comprising less than 1000 nucleotides into a cell comprising contacting a composition according to the first aspect of the invention with the cell.

The fourth aspect of the invention provides a composition according to the first aspect of the invention for use in a method of medical treatment by therapy.

The final aspect of the invention provides a composition according to the first aspect of the invention for use in a method of treatment by therapy wherein nucleic acid comprising less than 1000 nucleotides is delivered into a cell.

The vesicles defined above are biocompatible and do not undergo any cytotoxic interactions with cells. They have improved delivery rates of nucleic acid in comparison to the delivery systems described in the prior art. Although mechanisms for delivering DNA into cells using block copolymers have already been disclosed, the delivery of nucleic acid comprising less than 1000 nucleotides in vesicles which preferably have a pH-dependent dissociation is described herein for the first time. The length of the nucleic acid has been shown to significantly influence its interaction with the copolymer. The methods described herein are suitable for delivery of small nucleic acid molecules.

DETAILED DESCRIPTION OF THE INVENTION

In the copolymers used in this invention, preferably one of the blocks comprises pendant groups having a $pK_a$ in the range 3.0 to 6.9. This means that once the vesicles are taken up into cells, they advantageously dissociate and release nucleic acid within the cell. Without wishing to be bound by theory the inventor believes that release of the nucleic acid within the cell can be explained by the following. Dissociation is promoted by pH sensitivity of the block copolymer. The mechanism of cell internalisation (endocytosis) involves engulfment within phospholipid membranes produced by endocytic organelles such as trafficking vesicles, phagosomes, or pinosomes (depending on the precise endocytic pathway). The endocytic organelle detaches from the cell membrane and takes the vesicles inside the cell for further processing. Regardless of the endocytic pathway, the internalised vesicles experience a reduction in local pH from pH 7.4 to pH 5-6 once inside the organelle. This pH drop is sufficient to trigger the transition from nucleic acid-loaded vesicles to nucleic acid-copolymer complex. As this transition is confined within a semi-permeable organelle membrane, the sudden increase in particle number corresponds to a large increase in osmotic pressure. This causes lysis of the lipid membrane, releasing the nucleic acid into the cell cytosol.

As detailed above, the hydrophobic or the hydrophilic block of the amphiphilic block copolymer preferably comprises pendant groups which have a $pK_a$ in the range 3.0 to 6.9. This confers "pH sensitivity" on the copolymer. By $pK_a$ is meant the pH where half of the pendant groups are ionised. $pK_a$ can be determined by a variety of methods including pH titration, followed by potentiometric titration, UV spectroscopy and Dynamic Light Scattering (DLS). An appropriate method should be selected to measure the $pK_a$ according to the copolymer which is being analysed and its solubility in the test media.

DLS is the particularly preferred method for measuring $pK_a$. As indicated in the paper by Du et al; J. Am. Chem. Soc 2005, 127, 17982-17983, the DLS signal from $PMPC_{25}$-b-$PDPA_{120}$ copolymer in water varies with pH. At a certain pH the signal rapidly increases as the copolymer undergoes a transition from being molecularly deassociated to associated. The $pK_a$ is taken as the pH of the mid-point of this rapid increase. These experiments are described further in Giacomelli et al, Biomacromolecules 2006, 7, 817-828. In this reference, the experiments are performed on micelles of PMPC-b-PDPA block copolymer, but the techniques may also be used when the phase transition involves vesicle formation.

In the specification, the $pK_a$ of a group in a polymer is determined on the basis of a polymer system (and not assumed to be the same as the $pK_a$'s of similar moieties in non-polymeric systems).

Typically, the hydrophobic block has the pendant groups with a $pK_a$ in the range 3.0 to 6.9. Preferably, the $pK_a$ of the pendant groups is in the range 4.0 to 6.9, more preferably 5.5 to 6.9. The vesicles are correspondingly capable of disassociating in such pH ranges.

It is preferred that the hydrophobic block comprise pendant cationisable moieties as pendant groups. Cationisable moieties are, for instance, primary, secondary or tertiary amines, capable of being protonated at pH's below a value in the range 3 to 6.9. Alternatively the group may be a phosphine.

The nucleic acid may be double or single stranded and may be DNA or RNA. Typically, the nucleic acid comprises less than 500 nucleotides and preferably has less than 200 nucleotides, more preferably less than 100 nucleotides. In one preferred embodiment, the nucleic acid is an oligonucleotide, which is defined herein as comprising 2-20 nucleotides. The nucleic acid may be a Locked Nucleic Acid (LNA). This is formed from modified RNA nucleotides.

The nucleic acid is preferably an "anti-sense" oligonucleotide, i.e. preferably has a base sequence which is complementary to the mRNA, of a gene of interest, which is called the "sense" sequence. For instance, the nucleic acid may be anti-sense DNA.

Anti-sense molecules can be classified as "enzyme-dependent" or "steric blocking". Enzyme-dependent anti-sense include forms dependent on RNase H activity to degrade target mRNA, including ssRNA, RNA and phosphorothioate anti-sense. Steric blocking anti-sense interferes with gene expression or other mRNA-dependent cellular processes by binding to a target sequence of mRNA and sterically hindering gene expression. Steric blocking anti-sense molecules include peptide nucleic acid, locked nucleic acid and morpholino anti-sense.

Preferably, the nucleic acid is an RNA molecule, preferably an interfering RNA (iRNA) molecule.

iRNA is typically double stranded and may comprise 200 nucleotides or more. Typically, the iRNA comprises in the range 15 to 100 nucleotide pairs. Interfering RNA acts via a different mechanism to anti-sense RNA, but both achieve the same effect (gene silencing). Anti-sense RNA is typically single stranded, whereas interfering RNA operates via double stranded RNA fragments which trigger catalytically mediated gene silencing, most typically by targeting the RNA-induced silencing complex to bind to and degrade the mRNA.

Preferably, the iRNA molecule is a small interfering RNA molecule (siRNA). siRNA typically consist of a double-stranded RNA structure which comprises between 15 to 25, preferably 18 to 23 nucleotide pairs which are base-pairing to each other, i.e. are essentially complementary to each other, typically mediated by Watson-Crick base-pairing. One strand of this double-stranded RNA molecule is essentially complementary to a target nucleic acid, preferably a mRNA, whereas the second strand of said double-stranded RNA molecule is essentially identical to a stretch of said target nucleic acid.

The iRNA or siRNA molecule may be flanked on each side and each stretch, respectively, by a number of additional oligonucleotides which, however, do not necessarily have to base-pair to each other.

The composition of this invention is normally aqueous and typically therefore the vesicles are in aqueous solution. A typical pH of the aqueous composition is 7.0 to 7.6, preferably 7.2 to 7.4. Vesicles are generally substantially spherical and comprise a bilayered membrane. The bilayer is generally formed from two layers of amphiphilic molecules, which align to form an enclosed core with hydrophilic head groups facing the core and the exterior of the vesicle, and hydrophilic tail groups forming the interior of the membrane.

A typical diameter of a substantially spherical vesicle is in the range 50-5000 nm. More typically, the diameter is in the range 50-1000 nm. Vesicles having a diameter in this range are normally termed "nanovesicles". The nanovesicles are preferably substantially spherical in shape. Typically, the nanovesicles have a number average diameter of less than 300 nm, preferably less than 250 nm, most preferably less than 200 nm or 150 nm. The thickness of the bilayer is generally between 2 to 50 nm, more typically between 5 and 20 nm. These dimensions can be measured by Transmission Electron Microscopy (T.E.M), and Small Angle X-ray Scattering (SAXS) (Battaglia et al; JACS 127, 8757 (2005)).

The nucleic acid is typically associated with the vesicles via physical or chemical interaction, such as electrostatic or hydrophobic attraction. Usually the nucleic acid is not covalently bound to the vesicles and is encapsulated within the vesicles via physical entrapment alone. Typically, the vesicles are nanovesicles and the nucleic acid is encapsulated with the aqueous core of the nanovesicles.

The composition of this invention is typically an aqueous composition and has a pH which is substantially neutral. At this pH the amphiphilic copolymer is uncharged and therefore the nucleic acid is bound to the structures via physical encapsulation, and not electrostatic interaction.

Several techniques can be used to demonstrate that nucleic acid is encapsulated in the vesicles, as opposed to the vesicles and the nucleic acid simply forming a nucleic acid-copolymer electrostatically bound complex. Transition electron microscopy (TEM) and Dynamic Light Scattering (DLS) performed on the composition of the invention at pH7 allows an observer to view the presence of discrete vesicles, typically nanovesicles. The form of the vesicles is not affected by the presence of nucleic acid. Zeta (Z)-potential measurements also have utility. Such measurements typically do not demonstrate any charge from the nucleic acid or copolymer under neutral conditions, which indicates that the nucleic acid is encapsulated. The use of these methods is described further in Giacomelli et al; Biomacromolecules 2006, 7, 817-828 and in Du et al; J. Am. Chem. Soc. 2005, 127, 17982-17983. The presence of nucleic acid within the vesicles can also be visualised using a fluorescent probe such as DAPI, which passes through the membrane of the vesicles and detects nucleic acid in the core.

Other molecules, such as fluorescent dyes may also be associated with the vesicles. Preferably, they too are encapsulated in the core. If the dye bonds to the nucleic acid, the dye may be used as a reporter molecule to localise the nucleic acid once encapsulated.

A suitable label for use in the present invention is any label which fluoresces when excited with electromagnetic radiation, and can be associated with the self-assembled structures. Typically, the fluorescent label is encapsulated within the aqueous core of vesicles. However, when the fluroescent label is hydrophobic, more typically it is associated with the hydrophobic membrane. Fluorescent dyes, such as rhodamine, fluorescein, BODIPY® and NBD are particularly suitable.

In one embodiment of the invention, the hydrophobic block has a degree of polymerisation of at least 50, more preferably at least 70. Preferably, the degree of polymerisation of the hydrophobic block is no more than 250, even more preferably, no more than 200. Typically, the degree of polymerisation of the hydrophilic block is at least 15, more preferably at least 20. It is preferred that the ratio of the degree of polymerisation of the hydrophilic to hydrophobic block is in the range 1:2.5 to 1:8. All of these limitations promote vesicle, rather than micelle formation.

The hydrophobic and the hydrophilic block should be selected with regard to the $pK_a$ requirement for the pendant blocks.

In the invention, although the hydrophilic block may be based on condensation polymers, such as polyesters, polyamides, polyanhydrides, polyurethanes, polyethers (including polyalkylene glycols), polyimines, polypeptides, polyureas, polyacetals or polysaccharides, preferably the hydrophilic block is based on a radical polymerised addition polymer of ethylenically unsaturated monomers. Generally the monomers from which the block is formed themselves have zwitterionic pendant groups which remain unchanged in the polymerisation process. It may alternatively be possible to derivatise a functional pendant group of a monomer to render it zwitterionic after polymerisation.

Preferably, the hydrophilic block is formed from ethylenically-unsaturated zwitterionic monomers. Suitable ethylenically unsaturated zwitterionic monomers have the general formula $$Y\ B\ X \qquad\qquad\qquad I$$

In which Y is an ethylenically unsaturated group selected from $H_2C=CR—CO-A-$, $H_2C=CR—C_6H_4-A^1-$, $H_2C=CR—CH_2A^2$, $R^2O—CO—CR=CR—CO—O$, $RCH=CH—CO—O—$, $RCH=C(COOR^2)CH_2—CO—O$,

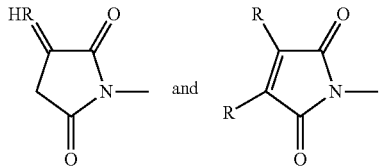

and

A is —O— or $NR^1$;
$A^1$ is selected from a bond, $(CH_2)_IA^2$ and $(CH_2)_I\ SO_3^-$ in which I is 1 to 12;
$A^2$ is selected from a bond, —O—, O—CO—, CO—O, CO—$NR^1$—, —$NR^1$—CO, O—CO—$NR^1$—, $NR^1$—CO—O—;
R is hydrogen or $C_{1-4}$ alkyl;
$R^1$ is hydrogen, $C_{1-4}$ alkyl or BX;
$R^2$ is hydrogen or $C_{1-4}$ alkyl;
B is a bond, or a straight branched alkanediyl, alkylene oxaalkylene, or alkylene (oligooxalkylene) group, optionally containing one or more fluorine substituents;
X is a zwitterionic group.

Preferably X is an ammonium, phosphonium, or sulphonium phosphate or phosphonate ester zwitterionic group, more preferably a group of the general formula II

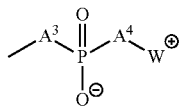

in which the moieties $A^3$ and $A^4$, which are the same or different, are —O—, —S—, —NH— or a valence bond, preferably —)—, and $W^+$ is a group comprising an ammonium, phosphonium or sulphonium cationic group and a group linking the anionic and cationic moieties which is preferably a $C_{1-12}$-alkanediyl group, preferably in which $W^+$ is a group of formula —$W^1$—$N^+$$R^3{}_3$, —$W^1$—$P^+R^4{}_3$, —$W^1$—$S^+R^4{}_2$ or —$W^1$-$Het^+$ in which:
$W^1$ is alkanediyl of 1 or more, preferably 2-6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^3$ are the same or different and each is hydrogen or alkyl of 1 to 4 carbon atoms, preferably methyl, or aryl, such as phenyl, or two of the groups $R^3$ together with the nitrogen atom to which they are attached form an aliphatic heterocyclic ring containing from 5 to 7 atoms, or the three groups $R^3$ together with the nitrogen atom to which they are attached as heteroaromatic ring having 5 to 7 atoms, either of which rings may be fused with another saturated or unsaturated ring to form a fused ring structure containing from 5 to 7 atoms in each ring, and optionally one or more of the groups $R^3$ is substituted by a hydrophilic functional group, and the groups $R^4$ are the same or different and each is $R^3$ or a group $OR^3$, where $R^3$ is as defined above; or Het is an aromatic nitrogen-, phosphorus- or sulphur-, preferably nitrogen-, containing ring, for example pyridine.

Monomers in which X is of the general formula in which $W^+$ is $W^1N^+R^3_3$ may be made as described in our earlier specification WO-A-9301221. Phosphonium and sulphonium analogues are described in WO-A-9520407 and WO-A-9416749.

Generally a group of the formula II has the preferred general formula III

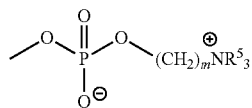

where the groups $R^5$ are the same or different and each is hydrogen or $C_{1-4}$ alkyl, and m is from 1 to 4, in which preferably the groups $R^5$ are the same preferably methyl.

In phosphobetaine based groups, X may have the general formula IV

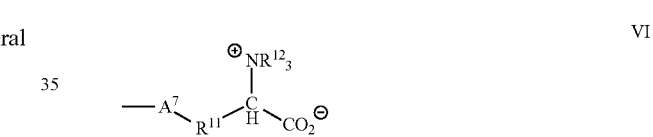

in which $A^5$ is a valence bond, —O—, —S— or —NH—, preferably —O—;

$R^6$ is a valence bond (together with $A^5$) or alkanediyl, —C(O)alkylene- or —C(O)NH alkylene preferably alkanediyl, and preferably containing from 1 to 6 carbon atoms in the alkanediyl chain;

$W^2$ is S, $PR^7$ or $NR^7$;

the or each group $R^7$ is hydrogen or alkyl of 1 to 4 carbon atoms or the two groups $R^7$ together with the heteroatom to which they are attached form a heterocyclic ring of 5 to 7 atoms;

$R^8$ is alkanediyl of 1 to 20, preferably 1 to 10, more preferably 1 to 6 carbon atoms;

$A^6$ is a bond, NH, S or O, preferably O; and $R^9$ is a hydroxyl, $C_{1-12}$ alkyl, $C_{1-12}$ alkoxy, $C_{7-18}$ aralkyl, $C_{7-18}$-aralkoxy, $C_{6-18}$ aryl or $C_{6-18}$ aryloxy group.

Monomers comprising a group of the general formula IV may be made by methods as described in JP-B-03-031718, in which an amino substituted monomer is reacted with a phospholane.

In compounds comprising a group of the general formula IV, it is preferred that $A^5$ is a bond;

$R^6$ is a $C_{2-6}$ alkanediyl;

$W^2$ is $NR^7$;

each $R^7$ is $C_{1-4}$ alkyl;

$R^8$ is $C_{2-6}$ alkanediyl;

$A^6$ is O; and $R^9$ is $C_{1-4}$ alkoxy.

Alternatively X may be a zwitterion in which the anion comprises a sulphate, sulphonate or carboxylate group.

One example of such a group is a sulphobetaine group, of the general formula V

where the groups $R^{10}$ are the same or different and each is hydrogen or $C_{1-4}$ alkyl and s is from 2 to 4.

Preferably the groups $R^{10}$ are the same. It is also preferable that at least one of the groups $R^{10}$ is methyl, and more preferable that the groups $R^{36}$ are both methyl.

Preferably s is 2 or 3, more preferably 3.

Another example of a zwitterionic group having a carboxylate group is an amino acid moiety in which the alpha carbon atom (to which an amine group and the carboxylic acid group are attached) is joined through a linker group to the backbone of the biocompatible polymer. Such groups may be represented by the general formula VI

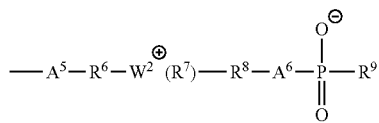

in which $A^7$ is a valence bond, —O—, —S— or —NH—, preferably —O—, $R^{11}$ is a valence bond (optionally together with $A^7$) or alkanediyl, —C(O)alkylene- or —C(O)NHalkylene, preferably alkanediyl and preferably containing from 1 to 6 carbon atoms; and the groups $R^{12}$ are the same or different and each is hydrogen or alkyl of 1 to 4 carbon atoms, preferably methyl, or two or three of the groups $R^{12}$, together with the nitrogen to which they are attached, form a heterocyclic ring of from 5 to 7 atoms, or the three group $R^{12}$ together with the nitrogen atom to which they are attached form a fused ring heterocyclic structure containing from 5 to 7 atoms in each ring.

Another example of a zwitterion having a carboxylate group is a carboxy betaine —$N^+(R^{13})_2(CH_2)_rCOO$— in which the $R^{13}$ groups are the same or different and each is hydrogen or $R_{1-4}$ alkyl and r is 2 to 6, preferably 2 or 3.

In the zwitterionic monomer of the general formula I it is preferred that the ethylenic unsaturated group Y is $H_2C=CR$—CO-A-. Such acrylic moieties are preferably methacrylic, that is in which R is methyl, or acrylic, in which R is hydrogen. Whilst the compounds may be (meth)acrylamido compounds (in which A is $NR^1$), in which case $R^1$ is preferably hydrogen, or less preferably, methyl, most preferably the compounds are esters, that is in which A is O.

In monomers of the general formula I, especially where Y is the preferred (alk)acrylic group, B is most preferably an alkanediyl group. Whilst some of the hydrogen atoms of such group may be substituted by fluorine atoms, preferably B is an unsubstituted alkanediyl group, most preferably a straight chain group having 2 to 6 carbon atoms.

A particularly preferred zwitterionic monomer is 2-methacryloyloxyethyl-phosphorylcholine (MPC). Mixtures of zwitterionic monomers each having the above general formula may be used.

The hydrophobic block may be formed of condensation polymers, such as polyethers (including polyalkylene glycols), polyesters, polyamides, polyanhydrides, polyurethanes, polyimines, polypeptides, polyureas, polyacetals, or polysiloxanes. One example of a suitable hydrophobic block is polyalkylene oxide, usually polypropylene oxide, that is the same type of block as has been used in the well-studied Pluronic/Poloxamer based systems. One type of highly hydrophobic block is poly(dimethylsiloxane). In one preferred embodiment the type of polymer forming the hydrophobic block is the same as that forming the hydrophilic block. Preferably the polymer is formed by radical polymerisation of ethylenically unsaturated monomers.

Suitable monomers from which the hydrophobic block may be formed have the general formula VII $Y^1B^1Q$     VII in which $Y^1$ is selected from $H_2C=CR^{14}—CO-A^8-$, $H_2C=CR^{14}—C_6H_4-A^9-$, $H_2C=CR^{14}—CH_2A^{10}$, $R^{16}O—CO—CR^{14}=CR^{14}—CO—O$, $R^{14}CH=CH—CO—O—$, $R^{14}CH=C(COOR^{16})CH_2—CO—O$,

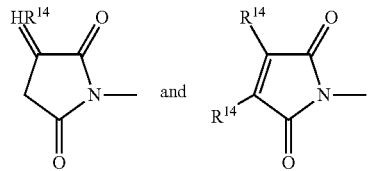

and $A^8$ is —O— or $NR^{15}$;

$A^9$ is selected from a bond, $(CH_2)_qA^{10}$ and $(CH_2)_q SO_3—$ in which q is 1 to 12;

$A^{10}$ is selected from a bond, —O—, O—CO—, CO—O—, CO—$NR^{15}$—, —$NR^{15}$—CO—, O—CO—$NR^{15}$—, $NR^{15}$—CO—O—;

$R^{14}$ is hydrogen or $C_{1-4}$ alkyl;

$R^{15}$ is hydrogen, $C_{1-4}$ alkyl or $B^1Q$;

$R^{16}$ is hydrogen or $C_{1-4}$ alkyl;

$B^1$ is a bond, or a straight branched alkanediyl, alkylene oxaalkylene, or alkylene (oligooxalkylene) group, optionally containing one or more fluorine substituents; and Q is a cationic or cationisable group of the formula —$NR^{17}_p$, —$PR^{17}_p$ and $SR^{17}_r$, in which p is 2 or 3, r is 1 or 2, the groups $R^{43}$ are the same or different and each is selected from the group consisting of hydrogen, $C_{1-24}$ alkyl and aryl, or two of the groups $R^{17}$ together with the heteroatom to which they are attached from a 5 to 7 membered heterocyclic ring or three $R^{17}$ groups together with the heteroatom to which they are attached form a 5 to 7 membered heteroaromatic ring, either of which rings may be fused to another 5 to 7 membered saturated or unsaturated ring, and any of the $R^{43}$ groups may be substituted by amino or hydroxyl groups or halogen atoms, wherein if p is 3, at least one of the groups $R^{17}$ must be halogen.

Preferably $Y^1$ is $H_2C=CR^{14}—CO-A^8-$ where $R^{14}$ is H or methyl and $A^8$ is O or NH.

Preferred groups $B^1$ are alkanediyl, usually with linear alkyl chains and preferably having 2 to 12 carbon atoms, such as 2 or 3 carbon atoms.

Preferably Q is $NR^{17}_2$ where $R^{17}$ is $C_{1-12}$-alkyl. Preferably both $R^{17}$'s are the same. Particularly useful results have been achieved where the groups $R^{17}$ are $C_{1-4}$ alkyl, especially ethyl, methyl or isopropyl.

Either or both the hydrophobic and hydrophilic blocks may include comonomers, for instance to provide functionality, control over hydrophobicity, control over pH sensitivity, $pK_{aH}$ or $pK_B$ as the case may be, control over temperature sensitivity or as general diluents. For instance comonomers providing functionality may be useful to provide conjugation of pendant groups following polymerisation and/or vesicle formation, to targeting moieties, or to provide for conjugation between the biologically active molecule and the polymer. Alternatively, functional groups may allow for crosslinking of the polymer following micelle formation, to confer increased stability on the micellar structure.

Examples of suitable comonomers are compounds of the general formula VIII

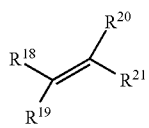

VIII in which $R^{18}$ is selected from hydrogen, halogen, $C_{1-4}$ alkyl and groups $COOR^{22}$ in which $R^{22}$ is hydrogen and $C_{1-4}$ alkyl;

$R^{19}$ is selected from hydrogen, halogen and $C_{1-4}$ alkyl;

$R^{20}$ is selected from hydrogen, halogen, $C_{1-4}$ alkyl and groups $COOR^{22}$ provided that $R^{18}$ and $R^{20}$ are not both $COOR^{22}$; and $R^{21}$ is a $C_{1-10}$ alkyl, a $C_{1-20}$ alkoxycarbonyl, a mono-or di-($C_{1-20}$ alkyl) amino carbonyl, a $C_{6-20}$ aryl (including alkaryl) a $C_{7-20}$ aralkyl, a $C_{6-20}$ aryloxycarbonyl, a $C_{1-20}$-aralkyloxycarbonyl, a $C_{6-20}$ arylamino carbonyl, a $C_{7-20}$ aralkyl-amino, a hydroxyl or a $C_{2-10}$ acyloxy group, any of which may have one or more substituents selected from halogen atoms, alkoxy, oligo-alkoxy, aryloxy, acyloxy, acylamino, amine (including mono and di-alkyl amino and tri-alkylammonium in which the alkyl groups may be substituted), carboxyl, sulphonyl, phosphoryl, phosphino, (including mono- and di- alkyl phosphine and tri-alkylphosphonium), zwitterionic, hydroxyl groups, vinyloxycarbonyl and other vinylic or allylic substituents, and reactive silyl or silyloxy groups, such as trialkoxysilyl groups;

or $R^{21}$ and $R^{20}$ or $R^{21}$ and $R^{19}$ may together form —$CONR^{23}CO$ in which $R^{23}$ is a $C_{1-20}$ alkyl group.

It is preferred for at least two of the groups $R^{18}$, $R^{19}$, $R^{20}$, and $R^{21}$ to be halogen or, more preferably, hydrogen atoms. Preferably $R^{18}$ and $R^{19}$ are both hydrogen atoms. It is particularly preferred that compound of general formula X be a styrene-based or acrylic based compound. In styrene based compounds $R^{21}$ represents an aryl group, especially a substituted aryl group in which the substituent is an amino alkyl group, a carboxylate or a sulphonate group. Where the comonomer is an acrylic type compound, $R^{21}$ is an alkoxy-carbonyl, an alkyl amino carbonyl, or an aryloxy carbonyl group. Most preferably in such compounds $R^{21}$ is a $C_{1-20}$-alkoxy carbonyl group, optionally having a hydroxy substituent. Acrylic compounds are generally methacrylic in which case $R^{20}$ is methyl.

Preferably the comonomer is a non-ionic comonomer, such as a $C_{1-24}$ alkyl(alk)-acrylate or -acrylamide, mono- or di-hydroxy-$C_{1-6}$-alkyl(alk)-acrylate, or acrylamide, oligo($C_{2-3}$ alkoxy) $C_{2-18}$-alkyl (alk)-acrylate, or -acrylamide, styrene, vinylacetate or N-vinyllactam.

For optimum nanovesicle formation, the block copolymers should have controlled molecular weights. It is preferable for each of the blocks to have molecular weight controlled within a narrow band, that is, to have a narrow polydispersity. The polydispersity of molecular weight should, for instance, be less than 2.0, more preferably less than 1.5, for instance in the range 1.1 to 1.4.

In one embodiment of this invention, the monomer from which the hydrophobic block is formed 2-(diisopropylamino) ethyl methacrylate (DPA) or 2-(diethylamino)ethyl methacrylate (DEA). The hydrophobic block is generally not formed from DMA monomers. In another embodiment, the hydrophilic block is PMPC. Preferably, the copolymer is a PMPC-b-PDPA block copolymer.

Preferably, the block copolymer has general formula $PMPC_m$-b-$PDPA_n$, wherein m is in the range 15-30 (for instance, 25) and n is 50 to 180, preferably 100 to 160, more preferably 120 to 160.

The block copolymer may be a simple A-B block copolymer, or may be an A-B-A or B-A-B block copolymer (where A is the hydrophilic block and B is the hydrophobic block). It may also be an A-B-C, A-C-B or B-A-C block copolymer, where C is a different type of block. C blocks may, for instance, comprise functional, e.g. cross-linking or ionic groups, to allow for reactions of the copolymer, for instance in the novel compositions. Crosslinking reactions especially of A-C-B type copolymers, may confer useful stability on nanovesicles. Cross-linking may be covalent, or sometimes, electrostatic in nature. Cross-linking may involve addition of a separate reagent to link functional groups, such as using a difunctional alkylating agent to link two amino groups. The block copolymer may alternatively be a star type molecule with hydrophilic or hydrophobic core, or may be a comb polymer having a hydrophilic backbone (block) and hydrophobic pendant blocks or vice versa. Such polymers may be formed for instance by the random copolymerisation of monounsaturated macromers and monomers.

The details of the process for polymerising the monomers which are used in this invention are to be found on WO 03/074090, pages 15-24.

The living radical polymerisation process useful in this invention has been found to provide polymers of zwitterionic monomers having a polydispersity (of molecular weight) of less than 1.5, as judged by gel permeation chromatography. Polydispersities in the range 1.2 to 1.4 for the or each block are preferred.

An advantage of the present invention is that vesicles may be loaded with nucleic acid using a pH change system. In such a process, polymer is dispersed in aqueous liquid in ionised form, in which it solubilises at relatively high concentrations without forming vesicles. Subsequently the pH is changed such that some or all of the ionised groups become deprotonated so that they are in non-ionic form. At the second pH, the hydrophobicity of the block increases and vesicles are formed spontaneously.

The method of forming vesicles with encapsulated nucleic acid, wherein one of the blocks of the amphiphilic block copolymer is pH-sensitive, typically involves the following steps:
(i) dispersing the amphiphilic copolymer in an aqueous media;
(ii) acidifying the pH of the composition formed in step (i);
(iii) adding the nucleic acid to the composition; and
(iv) raising the pH to around neutral to encapsulate the nucleic acid.

This method preferably comprises a further, preliminary step wherein the amphiphilic copolymer is dissolved in an organic solvent in a reaction vessel and the solvent is then evaporated to form a film on the inside of the reaction vessel.

By "pH-sensitive", is meant that one of the blocks has a group which becomes protonated/deprotonated at a particular pH. This pH is preferably in the range 3.0-6.9. Preferably, one of the blocks, and typically the hydrophobic block comprises pendant groups which have a pKa in the range 3.0 to 6.9, for instance, 4.0 to 6.9. Step (ii), of acidifying the composition, typically reduces the pH to a value below the $pK_a$, of the pendant group.

In more detail, vesicles of the amphiphilic block copolymer are typically prepared by dissolving copolymer in an organic solvent, such as a 2:1 chloroform:methanol mix in a glass container. Solvent is then typically evaporated under vacuum leaving a copolymeric film deposited on the walls of the container. The film is then re-hydrated with an aqueous solution, for instance using phosphate buffer saline. The pH of the resultant suspension is decreased to a pH of around 2, to solubilise the film, and then increased to around 6. When a pH of around 6, is reached, nucleic acid is added. The pH is then increased to around neutral to encapsulate the nucleic acid. The dispersion may then be sonicated and extruded, for instance using a bench top extruder with 200 nm membranes.

Further steps in the method may be required in order to improve the encapsulation efficiency, particularly when the nucleic acid is RNA. This is because RNA only weakly interacts with the polymer at pH6. The further steps may include an extrusion step which breaks down the vesicles, and then allows them to reform in the presence of the RNA. This may be repeated several, e.g. 2-5 times, in order to increase the encapsulation efficiency.

An alternative method for forming vesicles with encapsulated nucleic acid involves forming empty vesicles (by the method detailed above), or other methods known in the art. Nucleic acid is then added to an aqueous composition of the vesicles and the resultant composition is mixed to promote nucleic acid uptake by the vesicles. Sonication, for instance, may promote nucleic acid uptake.

The vesicles used in the invention may be formed from two or more different block polymers. For instance, they may be formed from a block copolymer comprising a polyalkylene oxide hydrophilic block, and from a block copolymer which has a hydrophilic block formed from a zwitterionic monomer. In this embodiment, in the method of forming vesicles, a mixture of the two block copolymers will be used. A suitable mixture would be, for instance, a 75:25 ratio by weight of PMPC-PDPA and PEO-PDPA.

The introduction of nucleic acid into cells is a desirable goal clinically. siRNA has the ability to knock down almost any gene of interest. Disease progression often depends on the activity of multiple genes, and turning off the activity of a gene with a siRNA lead to a potential benefit.

The application file contains at least one drawing executed in color. Copies of this patent or patent application publication with color drawing(s) will be provided by the Office upon request and payment of the necessary fee.

The invention will now be illustrated by the following Examples and Figures, wherein.

Figure 5:
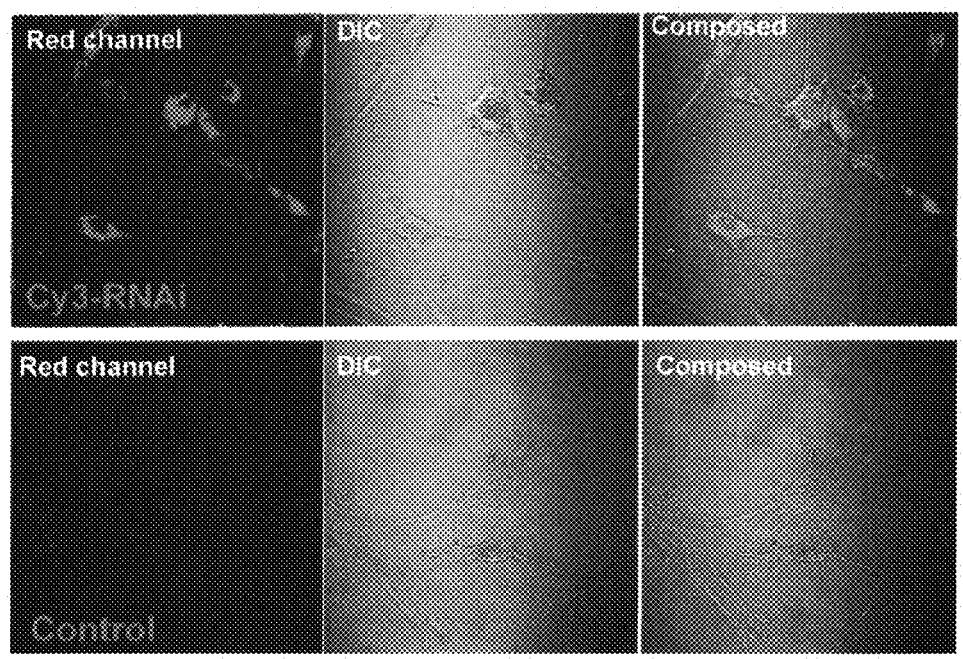
Figure 6:
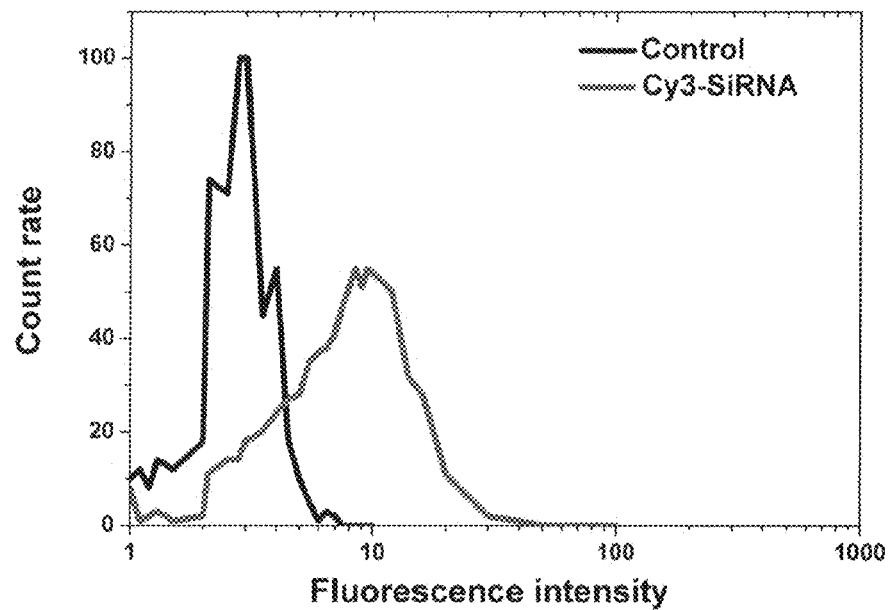
Figure 7:
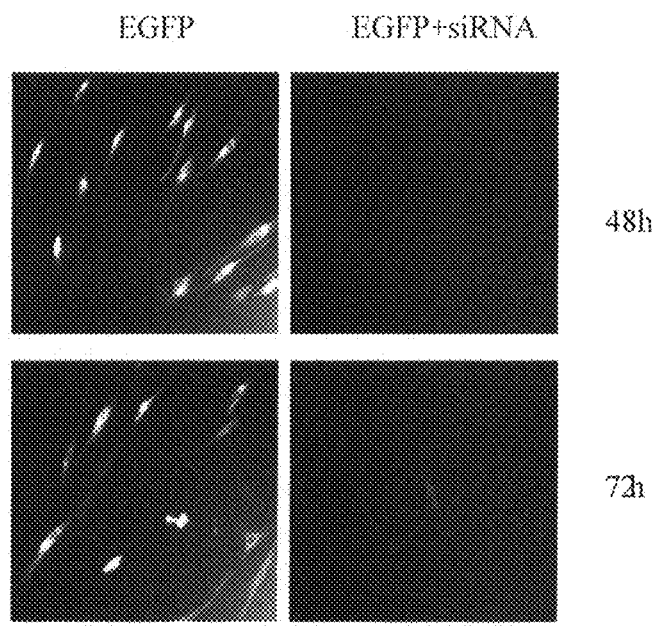
Figure 8:
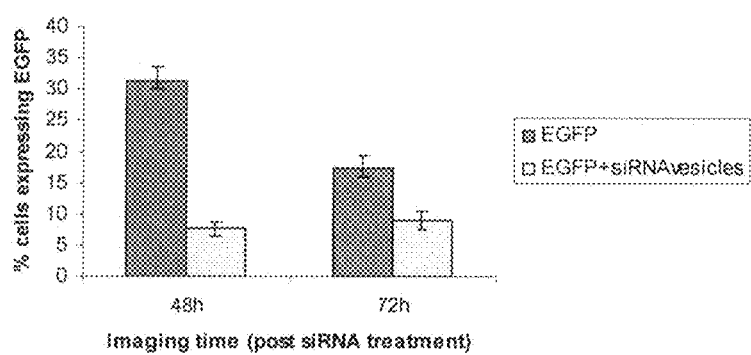
Figure 8:
Figure 9:
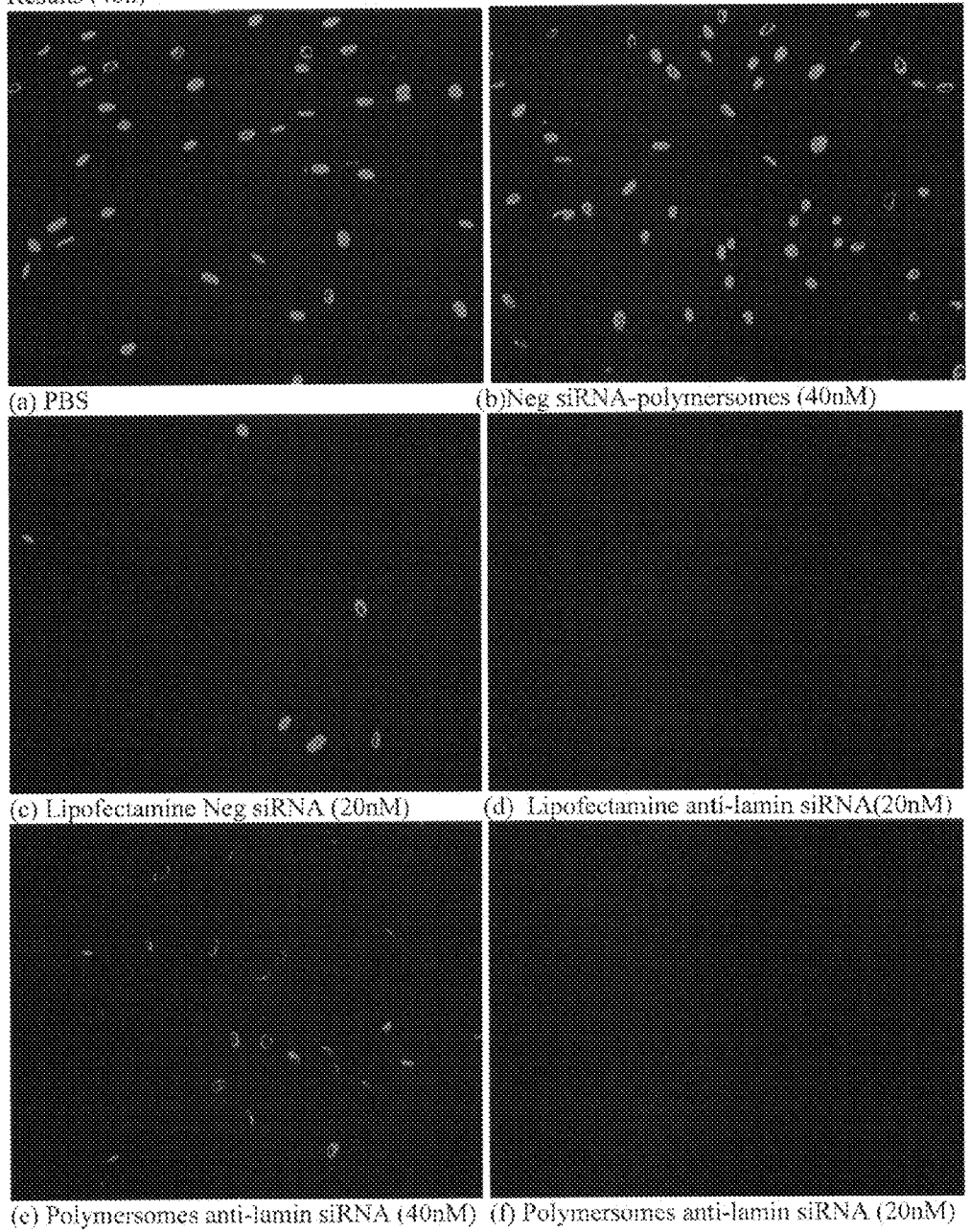
Figure 10:
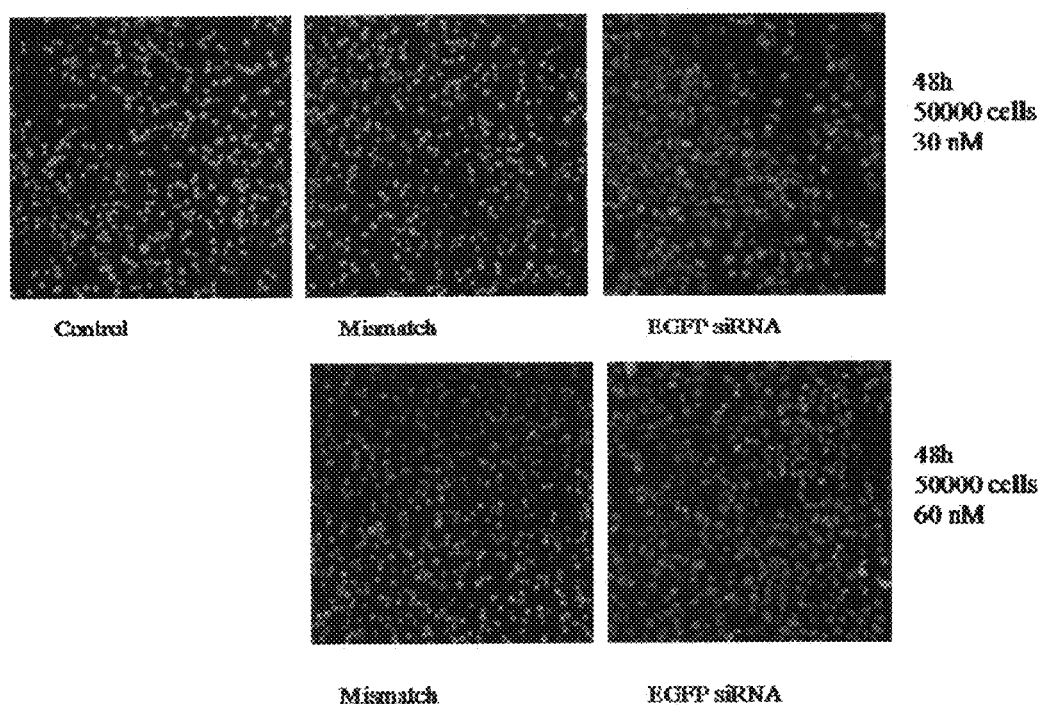
Figure 11:
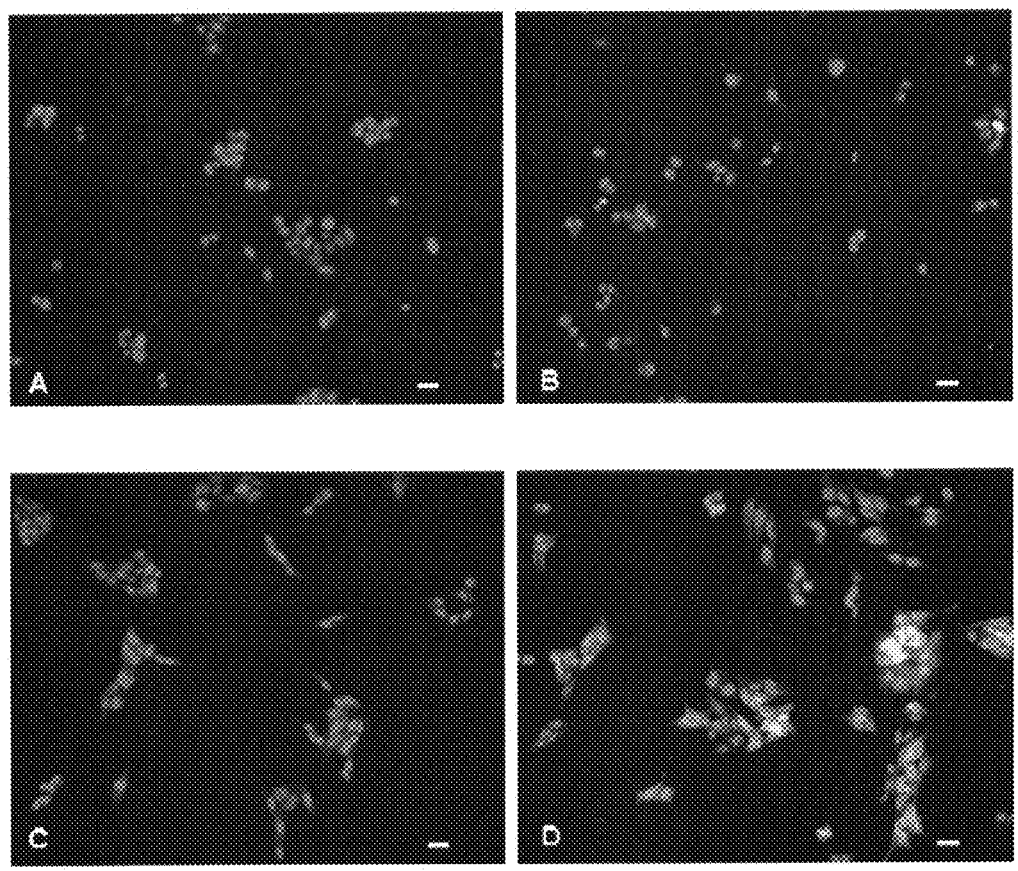
Figure 12:
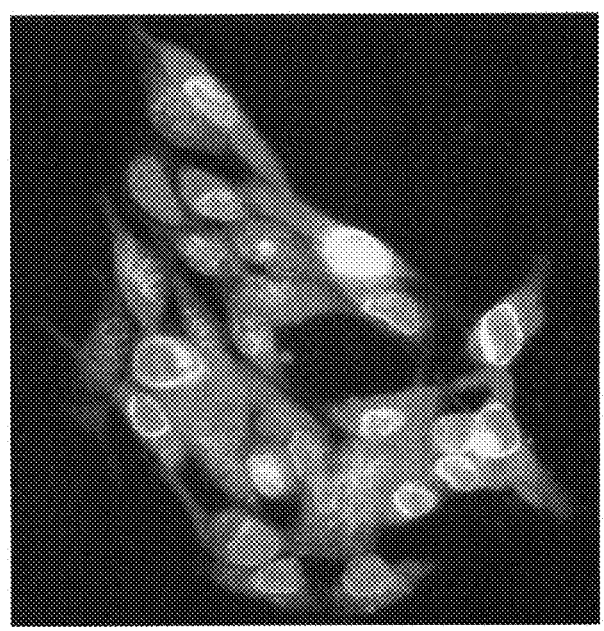
Figure 13:
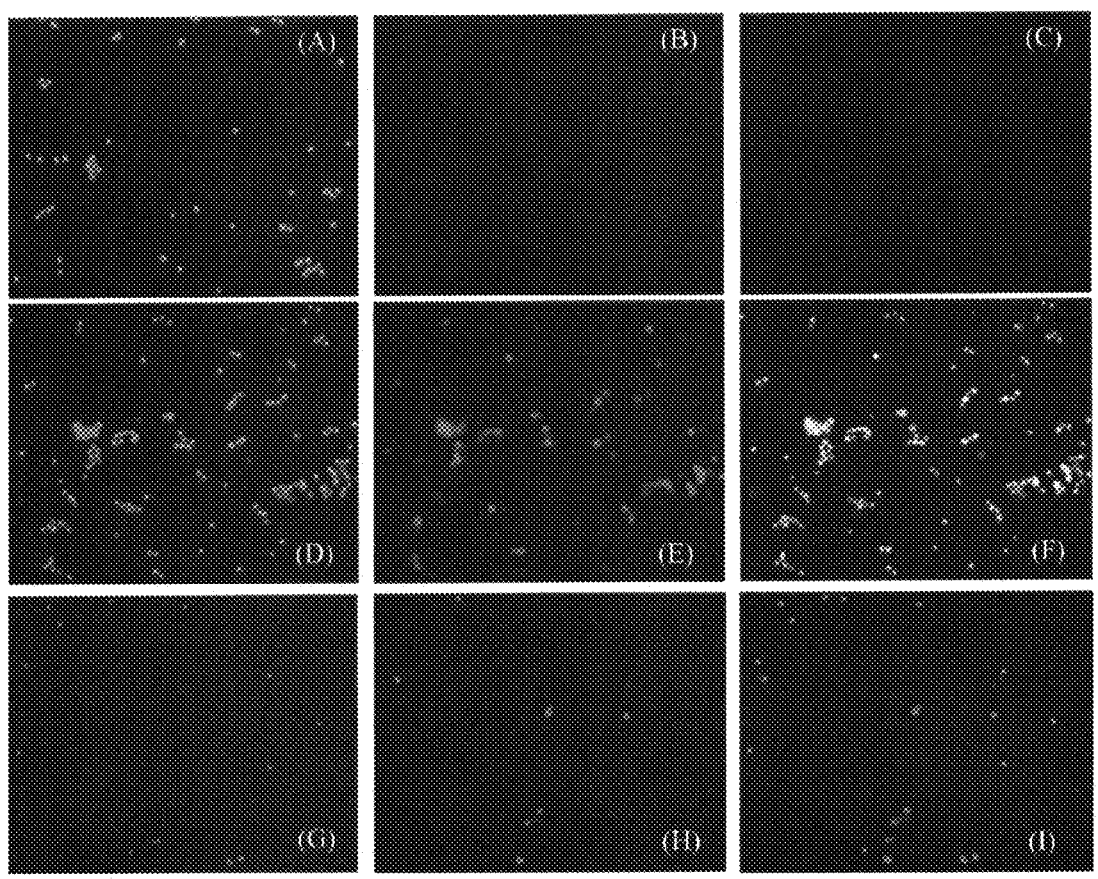
Figure 14:
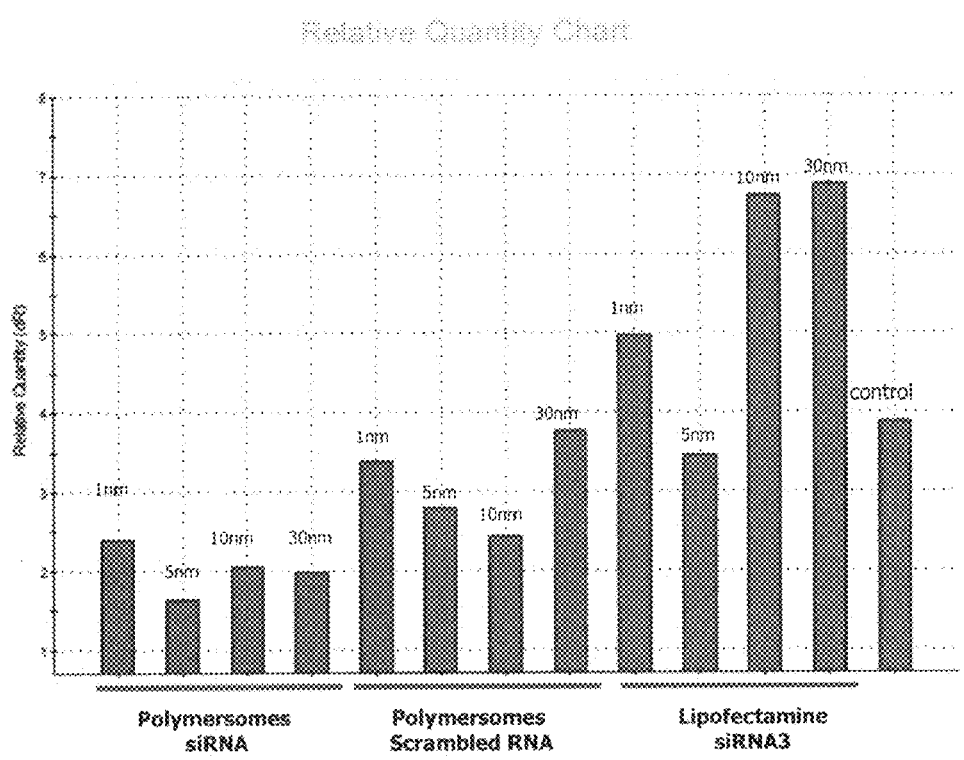
Figure 15:
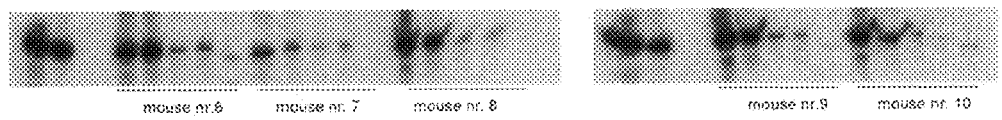
Figure 15:
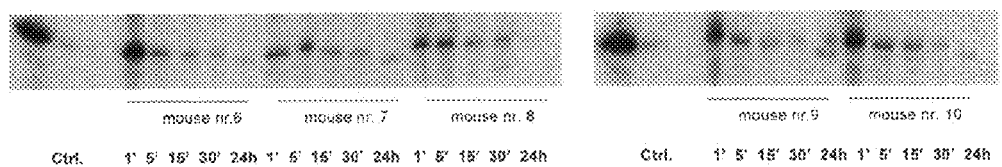
Figure 16:
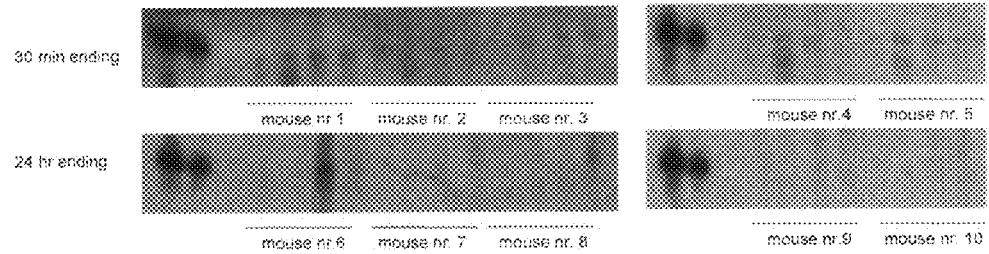
Figure 16:
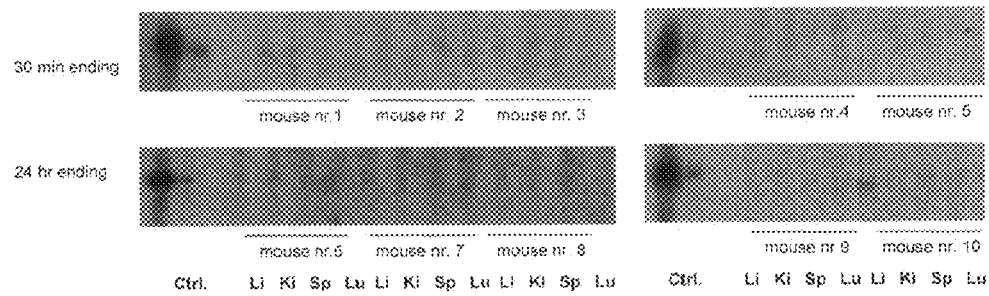
Figure 17A:
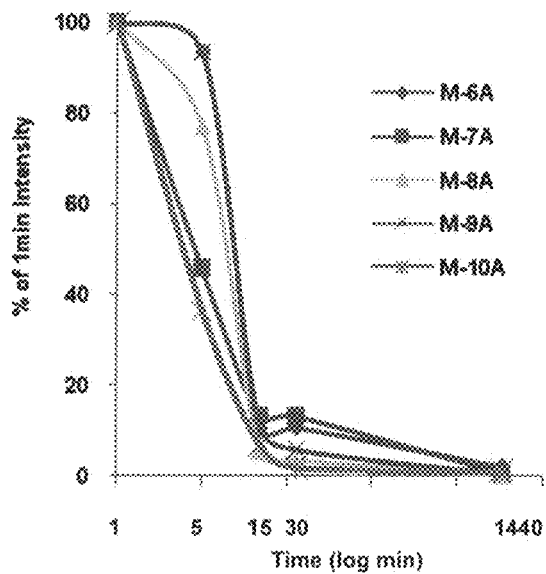
Figure 17B:
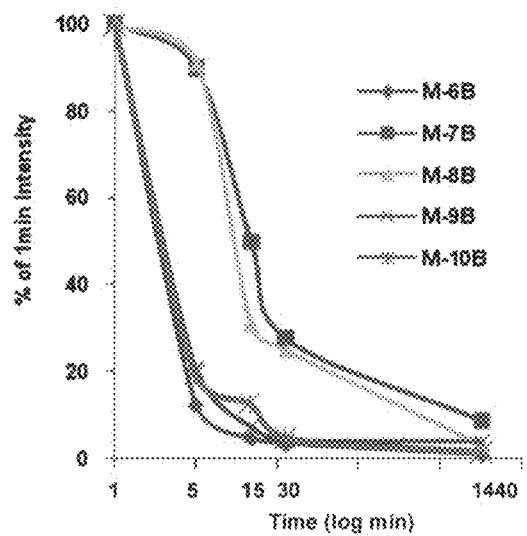

FIG. 5 contains Confocal Laser Scanning Micrographs that show the successful cytosolic polymersome-mediated delivery of fluorescently labelled (CY3) RNAi to Human Dermal Fibroblast (HDF) cells;

FIG. 6 shows Flow Cytometry data showing the successful cytosolic polymersome-mediated delivery of fluorescently labelled (CY3) RNAi to HDF cells;

FIG. 7 shows HDF cells transiently transfected with PEGFP and treated with EGFP siRNA containing polymeric vesicles;

FIG. 8 is a histogram showing the values for the green channel of the HDF cells of FIG. 7;

FIG. 9 shows fluorescent images of HDFs post immunolabelling of Lamin A/C after knock-down with polymersomes+ anti-Lamin siRNA (+controls);

FIG. 10 shows fluorescent images of H1299 cells 48 h post knock-down with 30 nM polymersomes+anti-EGFP;

FIG. 11 shows fluorescent images of a pituitary cell line at 1 h with (a) polymersomes alone; (b) polymersomes+Cy3-siRNA; 24 h with (c) polymersomes alone and (d) polymersome+Cy3-RNA;

FIG. 12 shows the fluorescent image of the 24, h incubation of polymersomes+Cy3-siRNA;

FIG. 13 shows fluorescent images of cell nuclei (A), (D), (G), siRNA (B), (E), (H) and merged images (C), (F), (I) for naked siRNA (A-C), polymersomes+siRNA (D-F) and Lipofectamine (G-I);

FIG. 14 shows real time PCR of relative quantity of ACTH produced post knock-down with polymersomes+siRNA3, vs polymersomes+scrambled siRNA with Lipofectamine and PBS controls;

FIG. 15 shows Northern Blot results of blood samples from 24 hr-ending mice with samples taken at 1 min, 5 min, 15 min, 30 min and 24 hours;

FIG. 16 shows Northern Blot results of organ samples from 30 min and 24 hr ending mice, with organs sampled: Liver (Li), Kidney (Ki), Spleen (Sp) and Lung (Lu);

FIG. 17*a*, shows LNA blood clearance results for particle A from 24 hr-ending mice; and FIG. 17*b*, shows LNA blood clearance results for particle B from 24 hr-ending mice.

EXAMPLE 1a

Procedure for the ATRP Synthesis of the PMPC$_{25}$-PDPA$_{70}$ Diblock Copolymer In a typical ATRP procedure, a Schlenk flask with a magnetic stir bar and a rubber septum was charged with Cu(I)Br (25.6 mg, 0.178 mmol) and MPC (1.32 g, 4.46 mmol). ME-Br initiator (50.0 mg, 0.178 mmol) and bpy ligand (55.8 mg, 0.358 mmol) were dissolved in methanol (2 mL), and this solution was deoxygenated by bubbling $N_2$ for 30 minutes before being injected into the flask using a syringe. The [MPC]:[ME-Br]:[CuBr]:[bpy] relative molar ratios were 25:1:1:2 and the reaction was carried out under a nitrogen atmosphere at 20° C. After 65 minutes, a deoxygenated mixture of DPA (2.67 g, 12.5 mmol, 70 eq.) and methanol (3 mL) were injected into the flask. After 48 h, the reaction solution was diluted by addition of isopropanol (about 200 mL) and then passed through a silica column to remove the catalyst. Typically, the yield would be 50-75% as some of the material is not easily recovered from the silica column.

Figure 1:
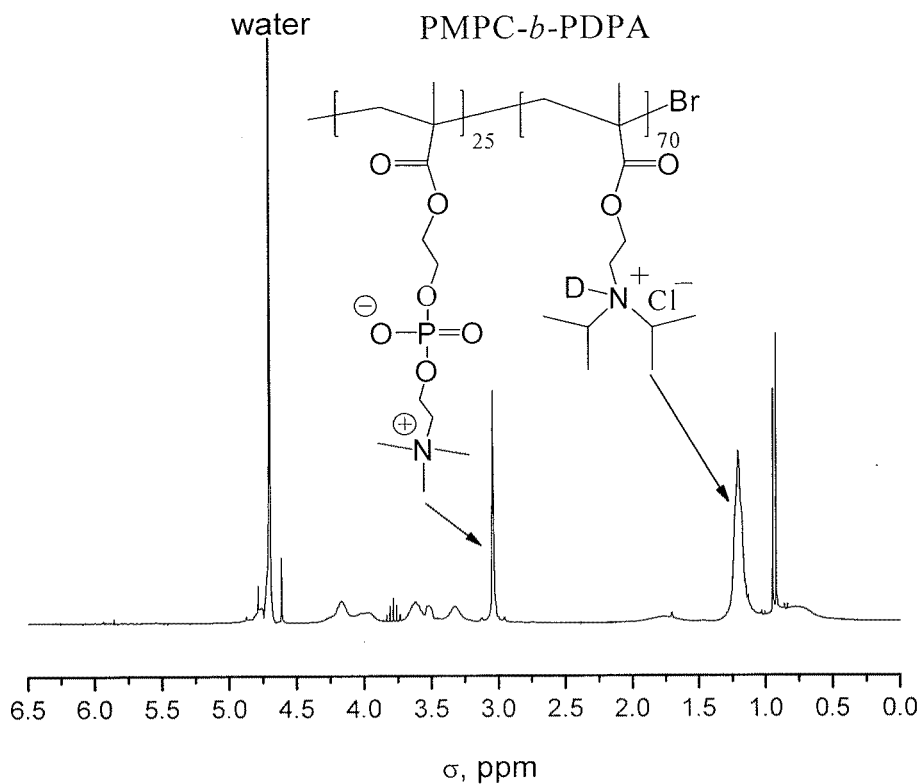
FIG. 1 is the $^1$HNMR spectrum carried out on the diblock copolymer formed in Example 1.
Figure 2:
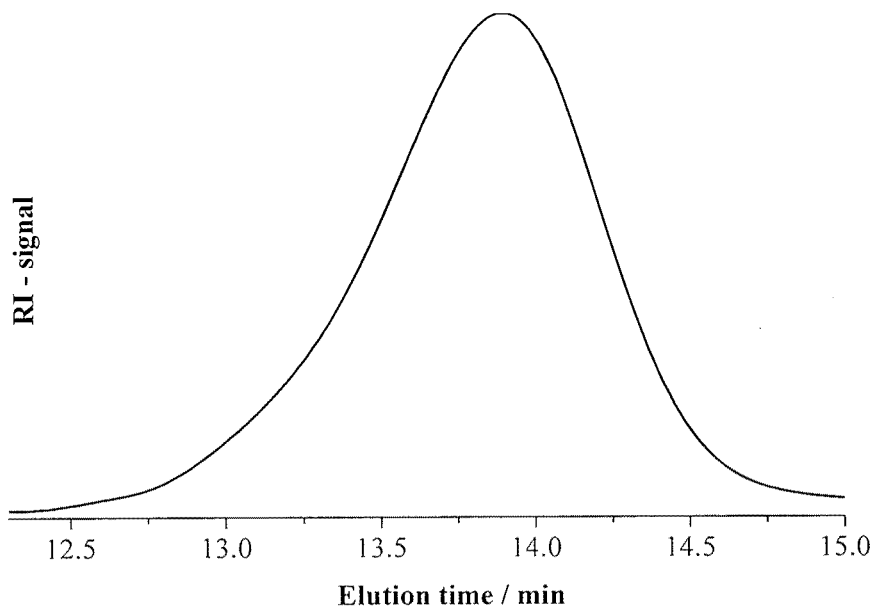
FIG. 2 is the Gel Permeation Chromatogram carried out on the diblock copolymer formed in Example 1.

Characterisation:

$^1$NMR was carried out at pH2 in $D_2O$ (see FIG. 1). GPC analysis of this diblock copolymer was conducted in a 3:1 chloroform/methanol mixture in the presence of 2.5 mM LiBr using poly(methyl methacrylate) standards (see FIG. 2). Typical results are presented in Table 1.

TABLE 1

Properties of the PMPC-PDPA diblock copolymer

| entry | Copolymer composition by $^1$H NMR in $D_2O$/DCl at pH 2 | $M_{n,GPC}$ | $M_w/M_n$ | TEM Morphologies |
|---|---|---|---|---|
| 1 | PMPC$_{25}$-PDPA$_{70}$ | 32,900 | 1.16 | vesicles + micelles |

EXAMPLE 1b

Synthesis of PEO-PDPA Copolymer

The procedure is based on that followed by Vamvakaki et al in Macromolecules; 1999; 32(6) pp 2088-2090.

The monohydroxy-capped poly(ethylene oxide) (PEO) was donated by Inspec U.K. GPC analyses gave Mw/Mn's of 1.10 for PEO; degrees of polymerization were either 22 or 45 for PEO. In a typical synthesis, PEO (5.0 g) dissolved in 100 mL of dry THF was added to a round-bottomed flask under dry nitrogen. Potassium naphthalene (2.50 mmol) in THF was added via a double-tipped needle, and the reaction solution was stirred at 30° C. for 1-2 h to form the alcoholate macroinitiator. Freshly distilled tertiary amine methacrylate (5-15 mL) was added, and the polymerization was allowed to proceed for 4 h prior to quenching with methanol. In some cases the polymerizations were conducted at 35 or 50° C. Solvent was removed under vacuum, the copolymer was redissolved in dilute HCl, and the water-insoluble naphthalene was removed by filtration. PEG$_{113}$-PDPA$_{71}$ and PEG$_{10}$-PDPA$_{30}$ were obtained in high yields (95-100%) with good control over copolymer molecular weight.

EXAMPLE 2

Generic Preparation of PC Polymersomes 20 mg of polymer described in Example 1 (PMPC$_{25}$-PDPA$_{70}$) was dissolved in 7.5 mL of a 2:1 chloroform:methanol mixture and the vial left open in a fumehood to evaporate completely and leave a thin film of polymer around the bottom of the vial. The polymer was dissolved by addition of 2 mL of PBS at pH2 to give a clear solution. The solution pH was raised to pH 6 at which point some turbidity resulted; this is the stage when the species to be encapsulated was added to the polymersome solution. The pH was then raised to pH 7.3 to induce polymersome closure and encapsulation of the species. The maximum concentration of polymer that should be used is around 10 mg/mL. Otherwise the structures that form interact with one another and discrete polymersomes do not form.

At this stage, 1 mL polymersomes corresponds to about 8 mg polymer. The polymersomes have a size in the order of 400 nm and the encapsulation efficiency around 5%. To improve on this, the solution was sonicated to induce break down and reformation of the polymersomes. The solution was put into a syringe and passed through a 200 nm extruder mesh which has been previously thoroughly cleaned in ethanol, into a receiver syringe. The solution was passed back and forth a minimum of 25 times. This improves encapsulation efficiency to ~20% and polymersome size is reduced to about 200 nm. The extruded material was passed again through the Sepharose column to remove the unencapsulated material. The eluant was collected in fractions every 100 μL and fraction % contained the polymersomes, as evident from the turbidity. The final volume collected increased from 1.2 to 1.4 mL. The polymersomes were then placed in the fridge and stored before use.

Characterisation:

Transmission Electron Microscopy. Samples were mounted on pre-coated carbon-coated copper grids. These grids were submerged for 20 seconds into the copolymer solution and then in uranyl formate water solution (2% w/w). Imaging was performed on a Philips CM100 instrument operating at 100 kV equipped with a Gatan 1 k CCD Camera.

Figure 3:
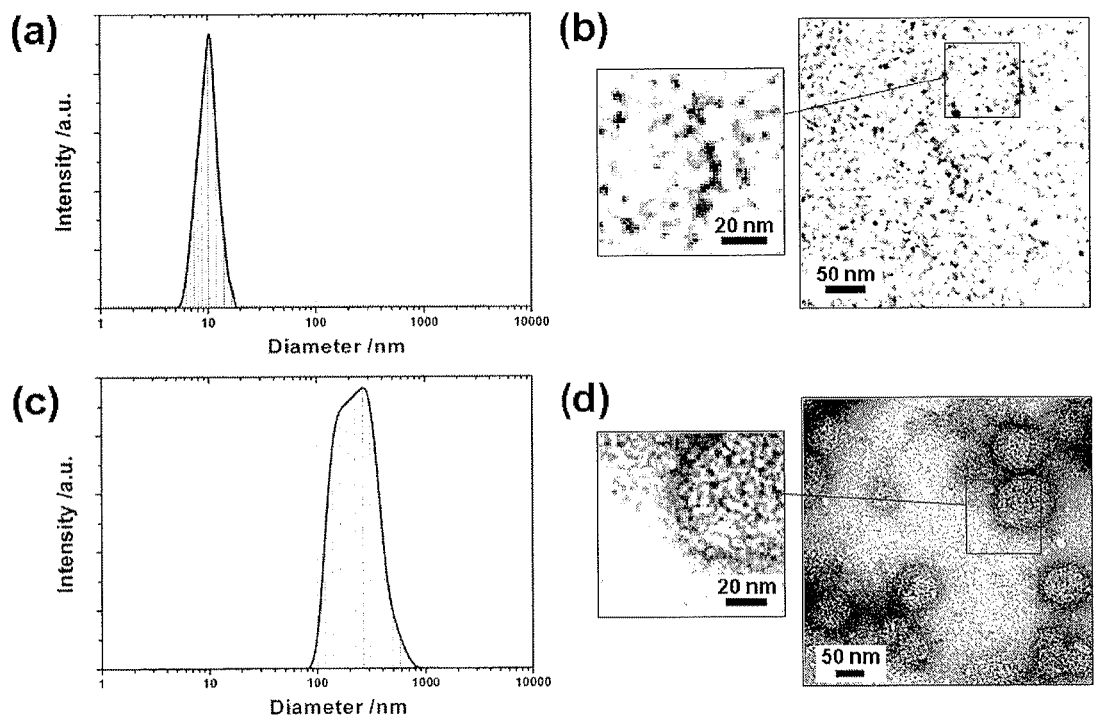
FIG. 3 shows (a) DLS particle size distribution of $PMPC_{25}$-$PDPA_n$ unimers at pH 6; (b) TEM micrograph of PMPC-PDPA unimers (polymer particles in unassembled form) at pH 6; (c) DLS particle size distribution of PMPC-PDPA polymersomes formed at pH 7; (d) TEM micrograph of the PMPC-PDPA polymersomes.

Dynamic Light Scattering (DLS). Dynamic light scattering measurements were performed on Brookhaven Instruments 200SM laser light scattering goniometer using a He—Ne 125 mW 633 nm laser. $PMPC_{25}$-$PDPA_{70}$ polymersome dispersions were diluted, if necessary, with filtered PBS to a concentration of 1 mg/ml and placed into glass vials. Single scans of ten minutes exposure were performed and particle sizes were estimated using the CONTIN multiple pass method of data analysis at angles of 30°, 90° and 120°. For analysis of the colloidal stability of the polymersomes with time, correlation between the average count rate histories and correlation functions at each angle were analyzed. FIG. 3 shows the results from TEM and DLS analysis on the polymer solution at different pHs.

EXAMPLE 3

Polymersome Stability on Storage

Figure 4:
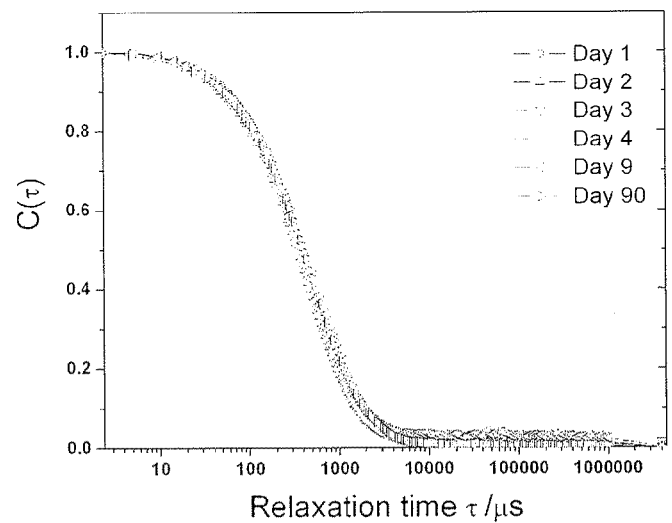
FIG. 4 shows PMPC-PDPA polymersome dispersion correlation function measured by DLS at different time points.

It was investigated using DLS whether storing the vesicles under different conditions affected their long term colloidal stability. The vesicles were stored at 5 mg/ml and 1 mg/ml, and stored at both room temperature and 5° C. for each of the concentrations. Measurements were taken on Day 1 (within 2 hours of the preparation of the vesicles), Day 2 (within 24 hrs of the preparation of the vesicles), Day 3 (within 48 hrs of the preparation of the vesicles), Day 4, Day 9 and Day 90. The graph in FIG. 4 shows that the correlation functions measured by DLS at different time points are almost identical indicating that the polymersomes' particle size distribution has not changed with time. They are therefore stable over an extended period, even at room temperature.

EXAMPLE 4

Encapsulation of siRNA Into Polymersomes

The block copolymer described in Example 1 self-assembles into vesicles at neutral pH, and dissolves completely as unimers at endocytic pH as described in Example 2. This transition can also be exploited for achieving efficient encapsulation of siRNA. Indeed, as the pH of the solution is still acidic the copolymers are dissolved molecularly. At this stage RNA can added to the solution and the pH is quickly raised. At neutral pH the vesicles start to form and therefore encapsulate the RNA within their aqueous core. Successful encapsulation can be demonstrated by a fluorescence assay based on the ability of diamidino-2-phenylindole (DAPI) to bind to nucleic acids. After encapsulation and GPC separation from the original solution, the RNA loaded polymersomes were added to primary human dermal fibroblast (HDF) cells. After 2 hours incubation the cells were analysed by confocal laser scanning microscopy (FIG. 5) which shows the presence of fluorescent siRNA distributed throughout the cytoplasm of the cell. Fluorescence flow cytometry (FIG. 6) demonstrates that the siRNA has been delivered to a large proportion of the cell population. Both techniques therefore confirm the efficient cytosolic delivery of Cy3 labelled RNA.

These data suggest that PMPC-PDPA polymersomes are able to efficiently encapsulate and deliver RNA within cell cytosols without affecting their viability. PMPC-PDPA polymersomes are therefore a valid alternative to lipid formulations.

EXAMPLE 5 siRNA Delivery With Polymeric Vesicles

Primary human dermal fibroblasts were transiently transfected (using the $CaPO_4$ method) with Plasmid Enhanced Green Fluorescent Protein (PEGFP) (from amaxa). Transfection efficiency was proven to be above 80% after 24 hrs. siRNA (from amaxa) was encapsulated in polymeric vesicles (37.5 micrograms/ml of vesicles) and added to transfected fibroblasts (1:10 dilution). Fluorescence micrographs were taken at $\lambda_{ex}$=495 nm/$\lambda_{em}$=515 nm for detection of EGFP expression at 48 h and 72 h. Optical micrographs of the same fields of views were taken to identify the total amount of cells per field of view. An N=1 experiment was performed with 6 samples per treatment.

FIG. 7 shows HDF cells transiently transfected with PEGFP and treated with EGFP siRNA containing polymeric vesicles. The siRNA treatment was performed for 24 hours and images were taken 48 and 72 h after treatment. The percentage of cells expressing EGFP was calculated with respect to the total number of cells per field of view in siRNA treated and untreated (EGFP control) groups. The degree of EGFP knockdown with the siRNA containing vesicles was calculated and normalised to the control (untreated group). EGFP production was considerably reduced with the treatment of vesicles containing EGFP siRNA (FIG. 8). The maximum of EGFP expression silencing was observed after 48 h treatment. A decrease in the expression was observed after 72 h, but this was less efficient than at 48 h. The vesicles containing the siRNA were stable (and effective) at 4 degrees Celsius for up to 5 days. Treatment with the vesicles did not alter the proliferative ability of the cells over the 72 h experimental time, as measured by nuclear counter labelling.

EXAMPLE 6

Knock-Down of Lamin A/C Using Polymersomes 1. siRNA Encapsulation

Lamins are intermediate filament-type proteins which form major components of the cellular nuclear lamina. The nuclear lamina is a matrix of protein located next to the inner nuclear membrane. In general terms, lamin proteins are involved in important cellular tasks such as nuclear stability, chromatin structure and gene expression. Mammals have two main type lamins, A and B. A type lamin A/C was used in this experiment.

Two 20 mg $PMPC_{20}$-$PDPA_{75}$ films were rehydrated with 4 ml PBS at pH2; filter sterilised and taken up to pH6. At this point the following samples were made:

1) Control polymersomes (1 mL of PMPC$_{20}$-PDPA$_{75}$ polymersome solution)
2) siRNA neg control (Ambion, cat #: AM4636) 5 µM (final volume: 1 mL of PMPC$_{20}$-PDPA$_{75}$ polymersome solution)
3) siRNA anti Lamin A/C (Ambion, cat #: AM 4619) 5 µM (final volume: 1 mL of PMPC$_{20}$-PDPA$_{75}$ polymersome solution)

Samples were taken up to pH 7, sonicated for 15 mins at 4° C. and passed through a GPC (Sepharose 4B) column under sterile conditions.

After the column, a picogreen curve was vesicleed using the control polymersome sample as diluent. The final concentration of siRNA encapsulated inside was calculated from a standard curve. The final concentration was approximately 500 nM, with an efficiency of 10%.

2. Knock-Down Experiments

HDF (human dermal fibroblast) cells were seeded on 96 well plates. After 24 hours, medium was replaced and cells were treated as follows:

siRNA-polymersomes (either negative control or anti-lamin A/C): siRNA final concentrations on cells of 40, 20, 10, 5 and 1 nM
Polymersomes empty (at concentrations of polymer equivalent to those ones used above)
PBS a (volumes equivalent to the ones used above)
Naked siRNA (at a concentration of 40 nM)
Lipofectamine control (negative control and anti-lamin siRNA, at a concentration of 20 nM, following manufacturer's instructions).

Experiments were performed in triplicate wells. Cells were incubated with the treatments for 24 h and afterwards, the transfectant medium was removed and cells were re-fed with new medium. After 48 h, the medium was removed, the monolayer washed with PBS and cells were fixed with 10% formalin for 1 h prior to immunolabelling.

3. Immunolabelling

Cell monolayers were washed a further three times in PBS, prior to cell permeabilisation with 0.1% Triton X100 for 20 minutes. Subsequently, cells were washed three times with PBS. Unreactive binding sites were blocked by adding a 5% dried milk powder solution to each well for 1 hour. A further three washes in PBS were performed prior to incubation with the first antibody solution. The first antibody (mouse monoclonal Jol 3 to Lamin A+C-Nuclear envelope marker, Abcam) was added at a concentration of 1:100 in 1% PBS-dried milk powder. Cells were incubated in the antibody solution at 4° C. for 18 hours. The cells were then washed three more times in PBS. Afterwards, cells were incubated for 1 hour at room temperature with rabbit polyclonal to mouse IgG-FITC (Abcam) in 1:1000 1% PBS-milk powder. Three further washes in PBS were performed. After this time, the fluorescent staining was visualised using an AXON image express system (Axon Instruments/Molecular Devices, Union City, Calif.). Briefly, fluorescence micrographs of immunolabelled samples were taken using epifluorescent illumination at $\gamma_{ex}$ 495 nm $\gamma_{em}$ 515 nm (for FITC visualisation).

Significant reductions in fluorescence were seen with 1-20 nM anti-Lamin polymersomes. Significant cell death occurred with lipofectamine with both neg siRNA and anti-Lamin siRNA (FIG. 9a-i).

EXAMPLE 7

Knock-Down of EGFP Using Polymersomes

H1299 cells with stable expression of Enhanced Green Fluorescent Protein (EGFP) plated at 25,000 or 50,000 cells/well in 12 well plates were exposed to a 30 nM or 60 nM concentration of polymersomes containing anti-EGFP siRNA, with mismatch RNA and PBS as controls. Some significant off-target effects were observed as a consequence of delivering high levels of RNA and either causing cell toxicity or hyperproliferation and over-expression. Off-target effects are the result of the SiRNA interfering with the expression or function of genes or proteins other than the target. Some off-target effects can be eliminated using lower concentrations of SiNRA. At 30 nM or 60 nM with 50,000 cells at 48 hrs, a 50% knock down of EGFP could be observed (FIG. 10).

EXAMPLE 8

Knock-Down of POMC Gene in Pituitary Cells Using Polymersomes

In a model of Cushing's Disease, the Propiomelanocortin hormone (POMC) gene was knocked-down using polymersomes containing siRNA3, reducing the expression of Adenocorticotropic hormone (ACTH) (both in pituitary cell lines and in tumour cells extracted from patients). The pituitary cells are very sensitive to transfection agents, lipofectamine causing >30% cell death in cell lines and 100% cell death in cells taken from patients. In FIG. 11, Cy3-labelled siRNA was encapsulated and delivered to the pituitary cell lines. The fluorescent images clearly show siRNA delivery into the cells (FIG. 11), with a very homogeneous distribution of the labelled RNA within the cytosol (FIG. 12). Naked siRNA is not delivered without a vector, and lipofectamine is toxic to the cells (FIG. 13). The siRNA was shown to remain stable for at least 8 days post encapsulation.

A knock-down experiment was performed on the pituitary cell line with real time PCR used to determine the relative quantity of ACTH being produced. Some off target effect was seen with Lipofectamine with increased expression due to toxicity. Polymersome with scrambled siRNA control produced some unexplained knock-down but the most effective knock-down was seen using Polymersomes+siRNA3 at 5 nM.

EXAMPLE 9

In Vivo Study of Polymersomes Containing LNA.

Non-fluorescent polymersomes and fluorescent polymersomes (covalently labelled with rhodamine) encapsulating Locked Nucleic Acid (LNA) were evaluated separately and labelled as particles A & B. Polymersomes were prepared as described in Example 2. The maximum injection volume possible for administration per mouse was 200 µL. Two groups of 10 mice were divided for evaluation of particle A and particle B.

Particle A: Non-fluorescent polymersomes with LNA. 5 mice per group. Amount of LNA per mouse 5 µg/200 µl.

Particle B: Rhodamine-fluorescent polymersomes. 5 mice per group. Amount of LNA per mouse 11.2 µg/160 µl.

Mice 1-5 were sacrificed 30 mins after injection on the tail vein. Mice 6-10 were sacrificed after 24 hours. Blood samples were collected with a Pasteur pipette by retro-orbital blood collection (no anaesthetized mice) from the orbital sinus behind the eyeballs. Sampling of blood was performed after 1 min, 5 mins, 15 mins, 30 mins and 24 hours.

Blood samples were placed into EDTA containing eppendorf tubes to stop coagulation. The early time points were added to 1 μl 0.1 M EDTA containing tubes. The end points at 30 mins and 24 hrs were collected into 2 μl 0.25M EDTA containing tubes.

Organ samples (at 30 min time point and 24 h) were taken from random distal areas (approx ¼ of the kidney and lung, ⅕ spleen and about 1/10 of liver). Organs were kept in eppendorf tubes containing RNAlater (T.M.) (Ambion) to stop RNA from degrading (lung and liver with 600 μl RNAlater (T.M.), spleen and kidney with 400 μl RNAlater (T.M.)). Organ samples were kept overnight at room temperature to permeabilise the RNAlater (T.M.) and then stored at 2-4° C.

LNA deposition within blood and organs was analysed by Northern blot analysis. For blood clearance analysis the intensity of the LNA signals was measured by Quantity ONE programme system.

The results from Northern blots showed both particles were present in the blood stream for at least 24 hours, hence demonstrating a long circulation time (FIGS. 16 and 17a+b). Northern blots of the organ samples revealed a relatively consistent delivery of RNA to liver, kidney, spleen and lungs for both particles in all animals (FIG. 16).

The invention claimed is:

1. A composition comprising nanovesicles and encapsulated within the aqueous core of the nanovesicles, nucleic acid comprising less than 1000 nucleotides, wherein the nanovesicles comprise an amphiphilic block copolymer having a hydrophilic block formed from 2-methacryloyloxy ethyl phosphorylcholine and a hydrophobic block formed from 2-(diisopropyl)amino ethyl methacrylate, wherein the degree of polymerisation of the hydrophilic block is about 20 to 25 and the degree of polymerisation of the hydrophobic block is about 70 to 75 and wherein the nucleic acid is siRNA.

2. A composition according to claim 1, wherein the nanovesicles have a diameter in the range 50-1000 nm.

3. A composition according to claim 1 wherein the nucleic acid is small iRNA and comprises 15 to 25 nucleotide pairs.

4. A method for forming a composition according to claim 1, wherein one of the blocks is pH sensitive, comprising the steps:
   (i) dispersing the amphiphilic block copolymer in an organic solvent;
   (ii) acidifying the pH of the composition formed in step (i);
   (iii) adding the nucleic acid to the composition; and
   (iv) raising the pH to around neutral to encapsulate the nucleic acid.

5. A method according to claim 4 comprising a preliminary step before step (i), wherein the amphiphilic block copolymer is dissolved in an organic solvent in a reaction vessel and the solvent is then evaporated to form a film on the inside of the reaction vessel.

6. An in vitro method of delivering nucleic acid comprising less than 1000 nucleotides into a cell comprising contacting a composition according to claim 1 with the cell.

7. A method of introducing nucleic acid comprising less than 1000 nucleotides into cells, comprising administering a composition according to claim 1 to a human or animal body.

8. A method of introducing nucleic acid comprising less than 1000 nucleotides into cells according to claim 7, wherein a nucleic acid which is small iRNA and comprises 15 to 25 nucleotide pairs is delivered into a cell.

* * * * *